US007666099B2

(12) United States Patent
Crumby

(10) Patent No.: US 7,666,099 B2
(45) Date of Patent: *Feb. 23, 2010

(54) MULTI-SYSTEM GAMING TERMINAL COMMUNICATION DEVICE

(75) Inventor: Hardy Lee Crumby, Fernley, NV (US)

(73) Assignee: IGT, Reno, NV (US)

( * ) Notice: Subject to any disclaimer, the term of this patent is extended or adjusted under 35 U.S.C. 154(b) by 265 days.

This patent is subject to a terminal disclaimer.

(21) Appl. No.: 11/071,687

(22) Filed: Mar. 2, 2005

(65) Prior Publication Data

US 2005/0148393 A1 Jul. 7, 2005

Related U.S. Application Data

(63) Continuation of application No. 09/690,925, filed on Oct. 17, 2000, now Pat. No. 6,875,110.

(51) Int. Cl.
A63F 9/24 (2006.01)
H04L 12/00 (2006.01)

(52) U.S. Cl. ................. 463/42; 370/359; 370/395.5

(58) Field of Classification Search ............. 463/42
See application file for complete search history.

(56) References Cited

U.S. PATENT DOCUMENTS

| 4,553,222 | A | | 11/1985 | Kurland et al. |
| 5,048,831 | A | | 9/1991 | Sides |
| 5,572,882 | A | | 11/1996 | Acres et al. |
| 5,643,086 | A | | 7/1997 | Alcorn et al. |
| 5,655,961 | A | | 8/1997 | Acres et al. |
| 5,664,778 | A | * | 9/1997 | Kikuchi et al. .......... 273/148 B |
| 5,740,075 | A | | 4/1998 | Bigham et al. |
| 5,741,183 | A | | 4/1998 | Acres et al. |
| 5,752,882 | A | | 5/1998 | Acres et al. |
| 5,761,647 | A | | 6/1998 | Boushy |
| 5,766,076 | A | | 6/1998 | Pease et al. |
| 5,770,533 | A | | 6/1998 | Franchi |
| 5,797,085 | A | | 8/1998 | Beuk et al. |
| 5,800,269 | A | * | 9/1998 | Holch et al. .................. 463/42 |
| 5,820,459 | A | | 10/1998 | Acres et al. |
| 5,823,879 | A | * | 10/1998 | Goldberg et al. .............. 463/42 |
| 5,836,817 | A | | 11/1998 | Acres et al. |

(Continued)

OTHER PUBLICATIONS

U. S. Provisional Appl. No. 60/094,068, filed Jul. 24, 1998, entitled: "Input Output Interface and Device Abstraction" (69 pages).

(Continued)

Primary Examiner—Dmitry Suhol
Assistant Examiner—Seng H. Lim
(74) Attorney, Agent, or Firm—Weaver Austin Villeneuve & Sampson LLP

(57) ABSTRACT

A gaming machine with a communication multiplexer device that allows communications between the gaming machine and one or more game service servers all within a single network interface is described. The single network interface may be a wireless or wired network interface. The communication multiplexer device converts messages in native communication protocols used by the gaming machine to a network communication protocol such as TCP/IP for transmission over the single wired or wireless network interface. The communication multiplexer is designed such that the gaming machine may receive messages that have been transmitted using the native communication protocols without modifying regulated gaming software on the gaming machine.

22 Claims, 6 Drawing Sheets

U.S. PATENT DOCUMENTS

| | | | |
|---|---|---|---|
| 5,876,284 A | | 3/1999 | Acres et al. |
| 5,999,808 A | | 12/1999 | LaDue |
| 6,001,016 A | * | 12/1999 | Walker et al. .................. 463/42 |
| 6,003,013 A | | 12/1999 | Boushy et al. |
| 6,097,721 A | | 8/2000 | Goody |
| 6,099,408 A | | 8/2000 | Schneier et al. |
| 6,104,815 A | | 8/2000 | Alcorn et al. |
| 6,106,396 A | | 8/2000 | Alcorn et al. |
| 6,149,522 A | | 11/2000 | Alcorn et al. |
| 6,162,122 A | | 12/2000 | Acres et al. |
| 6,178,510 B1 | | 1/2001 | O'Connor et al. |
| 6,183,362 B1 | | 2/2001 | Boushy |
| 6,270,410 B1 | | 8/2001 | DeMar et al. |
| 6,285,868 B1 | | 9/2001 | LaDue |
| 6,319,125 B1 | | 11/2001 | Acres |
| 6,345,294 B1 | | 2/2002 | O'Toole et al. |
| 6,366,217 B1 | | 4/2002 | Cunningham et al. |
| 6,383,076 B1 | * | 5/2002 | Tiedeken ..................... 463/40 |
| 6,488,580 B1 | | 12/2002 | Robb |
| 6,638,170 B1 | | 10/2003 | Crumby |
| 6,682,423 B2 | | 1/2004 | Brosnan et al. |
| 6,968,405 B1 | | 11/2005 | Bond et al. |
| 2002/0077175 A1 | * | 6/2002 | Jorasch et al. ................ 463/25 |
| 2004/0002385 A1 | * | 1/2004 | Nguyen ....................... 463/42 |

OTHER PUBLICATIONS

Sportack, Mark A., IP Routing Fundamentals Cisco Systems, Cisco Press, 1999.

Office Action dated Aug. 28, 2002 from U.S. Appl. No. 09/690,925.

Final Office Action dated Jan. 3, 2003 from U.S. Appl. No. 09/690,925.

Office Action dated Apr. 17, 2003 from U.S. Appl. No. 09/690,925.

Final Office Action dated Oct. 3, 2003 from U.S. Appl. No. 09/690,925.

Office Action dated May 5,2004 from U.S. Appl. No. 09/690,925.

Notice of Allowance dated Nov. 29, 2004 from U.S. Appl. No. 09/690,925.

Australian Examination Report dated Sep. 6, 2005 from Australian Application No. 79450/01.

Tyson, Jeff: How Internet Infrastructure Works, howstuffworks.com, htty://computer.howstuffworks.com/internet-infrastructure.htm/printable, printed Apr. 3, 2009.

Franklin, Curt: How Routers Work, howstuffworks.com, http://computer.howstuffworks.com/firewall.htm/printable, printed Apr. 3, 2009.

Tyson, Jeff: How Firewalls Work, howstuffworks.com, http://computer.howstuffworks.com/firewall.htm/printable, printed Apr. 3, 2009.

Pidgeon, Nick: How Ethernet Works, howstuffworks.com, http://computer.howstuffworks.com/ethernet.htm/printable, printed Apr. 3, 2009.

Australian Examination Report dated Nov. 25, 2008 from Australian Application No. 2006236084.

* cited by examiner

MULTI-SYSTEM GAMING TERMINAL COMMUNICATION DEVICE

CROSS-REFERENCE TO RELATED APPLICATIONS

This application is a continuation and claims priority from U.S. patent application Ser. No. 09/690,925 entitled "MULTI-SYSTEM GAMING TERMINAL COMMUNICATION DEVICE," filed Oct. 17, 2000, now U.S. Pat. No. 6,875,110 which is incorporated herein by reference in its entirety for all purposes.

BACKGROUND OF THE INVENTION

This invention relates to game playing services for gaming machines such as slot machines and video poker machines. More particularly, the present invention relates to methods of providing communication interfaces for game services such as cashless play systems, accounting systems, progressive systems and player tracking systems on gaming machines.

There are a wide variety of associated devices that can be connected to a gaming machine such as a slot machine or video poker machine. Some examples of these devices are lights, ticket printers, card readers, speakers, bill validators, ticket readers, coin acceptors, display panels, key pads, coin hoppers and button pads. Many of these devices are built into the gaming machine or components associated with the gaming machine such as a top box which usually sits on top of the gaming machine.

Typically, utilizing a master gaming controller, the gaming machine controls various combinations of devices that allow a player to play a game on the gaming machine and also encourage game play on the gaming machine. For example, a game played on a gaming machine usually requires a player to input money or indicia of credit into the gaming machine, indicate a wager amount, and initiate a game play. These steps require the gaming machine to control input devices, including bill validators and coin acceptors, to accept money into the gaming machine and recognize user inputs from devices, including key pads and button pads, to determine the wager amount and initiate game play. After game play has been initiated, the gaming machine determines a game outcome, presents the game outcome to the player and may dispense an award of some type depending on the outcome of the game.

The operations described above may be carried out on the gaming machine when the gaming machine is operating as a "stand alone" unit or linked in a network of some type to a group of gaming machines. As technology in the gaming industry progresses, more and more gaming services are being provided to gaming machines via communication networks that link groups of gaming machines to a remote computer that provides one or more gaming services. As an example, gaming services that may be provided by a remote computer to a gaming machine via a communication network of some type include player tracking, accounting, cashless award ticketing, lottery, progressive games and bonus games.

Typically, network gaming services enhance the game playing capabilities of the gaming machine or provide some operational advantage in regards to maintaining the gaming machine. Thus, network gaming services provided to groups of gaming machines linked over a communication network of some have become very desirable in the gaming industry. However, to justify the costs associated with the infrastructure needed to provide network gaming services, a certain critical number of gaming machines linked in a network of some type must utilize the service. Thus, many of the network gaming services are only provided at larger gaming establishments where a large number of gaming machines are deployed.

A progressive game network offering progressive game services is one example where a group of gaming machines are linked together to provide a network gaming service. The progressive game services enabled by the progressive game network increase the game playing capabilities of a particular gaming machine by enabling a larger jackpot than would be possible if the gaming machine was operating in a "stand alone" mode. The potential size of the jackpot increases as the number gaming machines connected in the progressive network is increased. The size of the jackpot tends to increase game play on gaming machines offering a progressive jackpot which out weighs the costs of the progressive game network. As another example, the cashless ticketing service streamlines the money handling procedures involving groups of gaming machines by reducing the amount of money which must be collected at each gaming machine. To justify the costs of cashless ticketing system, a certain number of gaming machines utilizing the cashless ticketing system must be linked together to realize the benefits of the reduced operating costs associated with cashless ticketing system.

A current barrier to increasing the number of network gaming services provided to groups of gaming machines is the complexity of the communication networks associated with providing those network gaming services. Within the gaming industry, the evolution of network gaming services has produced a gaming service network environment where each network gaming service is provided by utilizing a separate communicate network. Thus, to provide four network gaming services to a gaming machine, such as player tracking, bonus games, progressive games and cashless ticketing, four separate communication networks may be utilized.

One reason for the complex gaming service network environment in the gaming industry are stringent regulatory restrictions for gaming machines requiring a time consuming approval process of any software modification to regulated gaming software on a gaming machine such that each time the regulated gaming software on a particular gaming machine is modified the gaming machine must be re-approved before it is deployed for operations. The re-approval process involves testing and inspection of each gaming machine that has incurred software modifications to its regulated gaming software. The software on the gaming machine allowing network gaming services such as progressive games, bonus games, cashless ticketing and accounting typically is regulated gaming software requiring re-approval of the gaming machine each time any of this software is modified. The hardware approval process is typically much faster because once a particular piece of hardware has been approved by a gaming jurisdiction it may be installed on any number of gaming machines without submitting each gaming machine with the new hardware for re-approval. Thus, for the gaming industry, hardware solutions, such as adding a new network to provide an additional network gaming service, may be favored over software solutions, such as modifying software on the gaming machine to provide an additional network gaming service over an existing network. Another reason for the complex gaming service network environment in the gaming industry is that many network gaming services have been developed by different manufactures such that the communication hardware used to provide one network gaming service by one manufacturer is incompatible with the communication hardware used to provide a second network gaming service by another manufacturer.

FIG. 1 is block diagram of components used to provide four network game services to a gaming machine in an example of the current gaming network environment. In FIG. 1, the gaming machine 100 receives four network game services including accounting services, progressive game services, player tracking services and cashless play services. As is typical in the gaming industry, a separate remote computer, network hardware and connection scheme is used to provide each network gaming service. The remote computer, network hardware and connection scheme comprise a gaming service network for the network gaming service. Thus, the accounting services are provided by an accounting server 110, accounting network hardware 102 and an accounting network connection scheme 118 connecting the gaming machine 100 to the accounting server 110. The progressive game services are provided by a progressive game server 112, progressive network hardware 104 and a progressive network connection scheme 120 connecting the gaming machine 100 to the progressive game server 112. The player tracking services are provided by a player tracking server 114, player tracking network hardware 106 and a player tracking network connection scheme 122 connecting the gaming machine 100 to the player tracking server 114. The cashless play services are provided by a cashless play server 116, cashless play network hardware 108 and a cashless play network connection scheme 124 connecting the gaming machine 100 to the cashless play server 116.

For simplicity only one gaming machine is shown in FIG. 1. Typically, the network hardware for each gaming service server connects a group of gaming machines. For instance, in a casino, an accounting server 110 may communicate with hundreds of gaming machines located on the casino floor. In addition, the number and types of gaming services may vary from gaming machine to gaming machine. For example, on a casino floor, only a fraction of the gaming machines may be connected to a progressive game server 112 while nearly all of the gaming machines will be typically connected to the accounting server 110.

The network hardware including 102, 104, 106 and 108 and connections schemes including 118, 120, 122 and 124 may be implemented using communication methods and hardware that vary depending on the type gaming service or the manufacturer of the gaming service. For instance, the accounting network hardware 102 may include concentrators, translators and controllers while the cashless play network hardware 108 may include concentrators, translators, controllers and cash validation terminals. Communications between the gaming machine and the remote gaming server may be carried out using wires, coaxial cables, twisted pair cabling and fiber optics using an asynchronous serial communication protocol at baud rates between about 300 and 19,200.

Some of the network hardware used for each gaming service may require the use of additional hardware within the gaming machine. For example, for player tracking services, an interface board is usually provided within the gaming machine 100 which is connected via 122 to the player tracking network hardware. The interface board may use a particular communication protocol to communicate with the player tracking server. There are many different manufacturers of player tracking interface boards and the type of communication protocol used on each interface board varies from manufacturer to manufacturer. Also, a fiber optic network is often used to provide a connection to the progressive network. Thus, a fiber optic communication interface may be provided in each gaming machine.

Disadvantages of the current gaming network environment include: 1) disruptions to gaming operations when a new gaming service network is added, 2) the cost of installing an entirely new network each time a gaming service requiring a new network is added, 3) costs associated with maintaining a complex network involving multiple gaming service networks supported by different vendors and 4) difficulties associated with moving gaming machines connected to a complex network involving multiple gaming service networks (e.g. to reconfigure a casino floor). In view of the above, it would be desirable to provide a gaming communication system for gaming machines that reduces the complexity of the gaming network environment and reduces the costs associated with adding new gaming services to a gaming machine requiring a gaming service network.

SUMMARY OF THE INVENTION

This invention addresses the needs indicated above by providing to the gaming machine, a communication multiplexer device that allows communications between that gaming machine and one or more game service servers all within a single network interface. The single network interface may be a wireless or wired network interface. The communication multiplexer device converts messages in native communication protocols used by the gaming machine to a network communication protocol such as TCP/IP for transmission over a single wired or wireless network interface. The communication multiplexer is designed such that the gaming machine may receive messages that have been transmitted using the native communication protocols without modifying regulated gaming software on the gaming machine.

One aspect of the present invention provides a gaming machine. The gaming machine can be generally characterized as including: 1) a master gaming controller that controls a game played on the gaming machine and communicates with one or more game service servers wherein each game service server provides at least one game service; 2) a communication multiplexer device connected to the master gaming controller where the communication multiplexer device comprises: (i) one or more communication ports where each communication port transmits and receives messages with the master gaming controller using a native communication protocol, (ii) an output communication port that transmits and receives messages with the one or more game service servers using a second communication protocol, and (iii) processor logic that multiplexes and demultiplexes messages between the one or more communication ports and the output communication port and that converts between the native communication protocol and the second communication protocol and 3) a network interface connected to the output communication port that receives and transmits messages in the second communication protocol where the network interface is a wireless radio connection or a wired Ethernet connection. The gaming machine may include an antenna for transmitting and receiving communications over the wireless radio connection. In specific embodiments, the game service is selected from group consisting of progressive game services, bonus game services, player tracking services, cashless ticketing services, game downloading services, prize services, entertainment content services, concierge services, lottery services and money transfer services.

In one embodiment, the one or more communication ports may comprise a first communication port using a first native communication protocol a second communication port using a second native communication protocol where the native communication protocol is selected from the group consisting of a progressive game service protocol, a bonus game service protocol, a player tracking service protocol, a cashless ticketing service protocol, a game downloading service protocol, a prize service protocol, an entertainment content service protocol, a concierge service protocol, a lottery service protocol and a money transfer service protocol. A physical interface for the one or more communication ports may be selected from the group consisting of RS-422/485, Fiber Optic, RS-232, DCS Current Loop, Link Progressive Current Loop, FIREWIRE, Ethernet and USB. Also, the one or more communication ports may comprise a first communication port that receives and sends messages from a first game service server and a second communication port that receives and send messages from a second game service server where the communication between the gaming machine and the one or more game servers may be encrypted. The one or more game service servers may be selected from the group consisting of a prize server, a game server, an entertainment content server, a cashless ticketing server, progressive game server, a bonus game server, a concierge service server, a lottery server and a money transfer server.

In other embodiments, the processor logic configures each of the one or more communication ports to emulate a native communication protocol where the communication multiplexer communication device communicates with a boot server to determine the native communication protocol to be used on each of the one or more communication ports. The second communication protocol used by the multiplexer communication may be a TCP/IP communication protocol where the gaming machine employs regulated gaming software that provides messages in the native communication protocol and where the regulated gaming software is not modified to accept messages transmitted in the second communication protocol.

Another aspect of the present invention provides a multiplexer communication device for multiplexing communications between a gaming machine and one or more game service servers. The multiplexer communication device may be characterized as including: 1) one or more communication ports wherein each communication port transmits and receives messages between the gaming machine and the multiplexer communication device in a native communication protocol; 2) a multi-port communication board allowing each communication port to be configured to accept multiple native communication protocols; 3) an output communication port that transmits messages addressed to one or more game servers and receives messages from one or more game service servers addressed to one or more communication ports using a second communication protocol; and 4) processor logic that multiplexes and demultiplexes messages between the one or more communication ports and the output communication port and that converts between the native communication protocol and the second communication protocol. The communication multiplexer device may also include: a) an EEPROM that provides configuration information to the processor board, b) a firewall connected to the output communication port, c) a power supply d) an antenna connected to the output communication port and e) a network interface board where the network interface board provides a wireless radio network interface or a wire Ethernet network interface.

In specific embodiments, the second communication protocol may be a TCP/IP communication protocol and the native communication protocol may be selected from the group consisting of a progressive game service protocol, a bonus game service protocol, a player tracking service protocol, a cashless ticketing service protocol, a game downloading service protocol, a prize service protocol, an entertainment content service protocol, a concierge service protocol, a lottery service protocol and a money transfer service protocol. A physical interface for the one or more communication ports may be selected from the group consisting of RS-422/485, Fiber Optic, RS-232, DCS Current Loop, Link Progressive Current Loop, FIREWIRE, Ethernet and USB. The one or more communication ports may comprise 8 to 16 communication ports.

Another aspect of the present invention provides a method of providing communications between a gaming machine and one or more game service servers in a communication multiplexer device connected to the gaming machine. The method may be characterized as including: 1) establishing communications with a boot server located outside of the communications multiplexer device wherein the communication multiplexer device is assigned an IP address by the boot server; 2) initializing one or more communication ports; 3) mapping each communication port to a port game service server; 4) configuring each communication port to accept a native communication protocol used by the port game service server and the gaming machine; 5) establishing a communication connection between each communication port and the port game service server using a second communication protocol; and 5) for each communication port, transmitting a message from the port game service server to the gaming machine through the communication port. The method may also include: a) converting messages from the gaming machine in the native communication protocol received at one of the communication ports to the second communication protocol and transmitting the messages in the second communication protocol to the port game service server, b) converting messages from the port game server addressed to one of the communications ports in the second communication protocol to the native communication protocol of the communication port and transmitting the messages in the native communication protocol to the communication port, c) receiving a message from the port game service server wherein the message contains a communication port address and routing the message from the game service server to the communication port indicated by the communication port address and d) receiving a message from the gaming machine at one of the communication ports, determining an address of the game service server corresponding to the one communication port and routing the message from the gaming machine to the address of the game service server.

These and other features of the present invention will be presented in more detail in the following detailed description of the invention and the associated figures.

DESCRIPTION OF THE PREFERRED EMBODIMENTS

Figure 2:
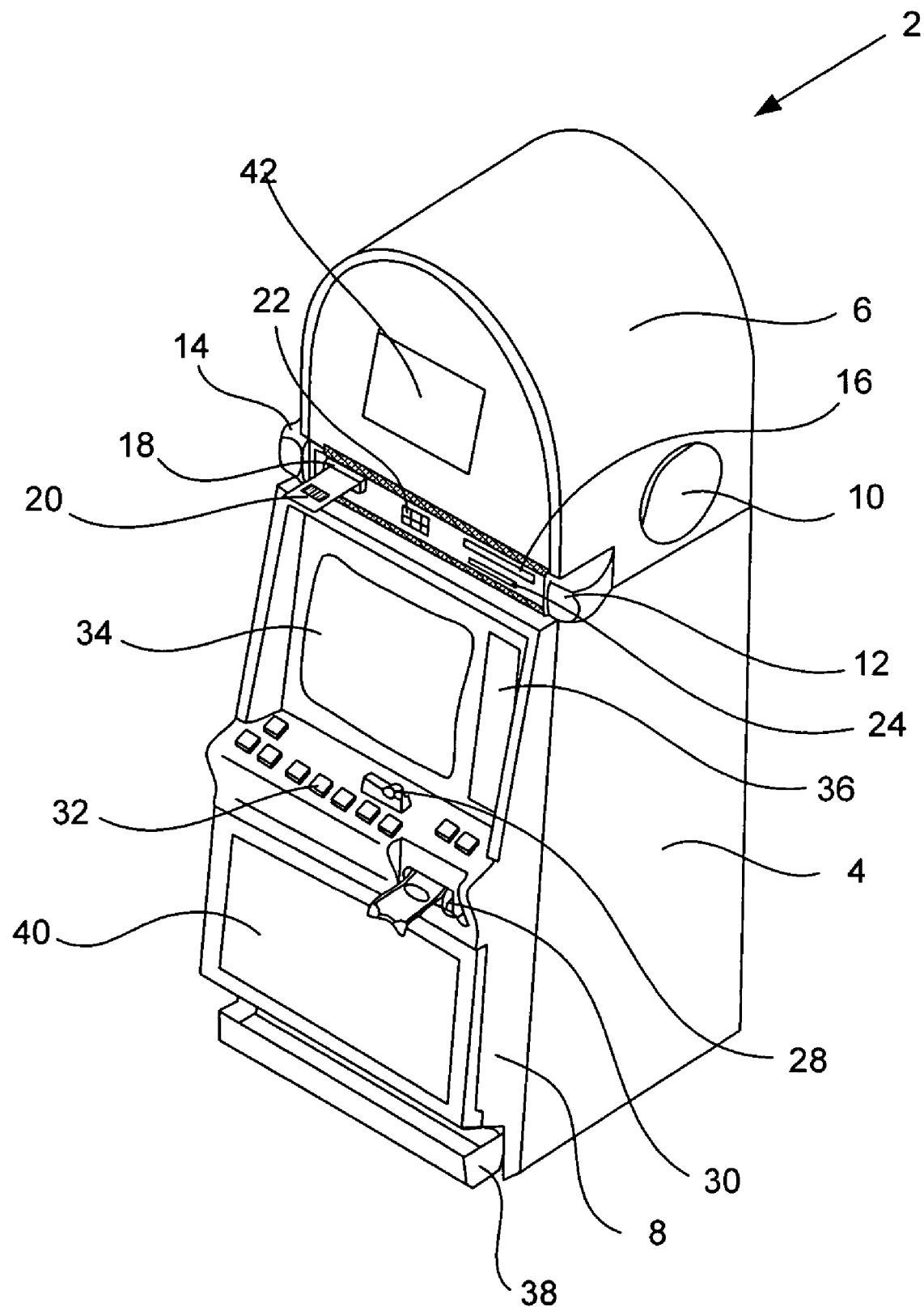
FIG. 2 is a perspective drawing of a gaming machine having a top box and other devices.

Turning first to FIG. 2, a video gaming machine 2 of the present invention is shown. Machine 2 includes a main cabinet 4, which generally surrounds the machine interior (not shown) and is viewable by users. The main cabinet includes a main door 8 on the front of the machine, which opens to provide access to the interior of the machine. Attached to the main door are player-input switches or buttons 32, a coin acceptor 28, and a bill validator 30, a coin tray 38, and a belly glass 40. Viewable through the main door is a video display monitor 34 and an information panel 36. The display monitor 34 will typically be a cathode ray tube, high resolution flat-panel LCD, or other conventional electronically controlled video monitor. The information panel 36 may be a back-lit, silk screened glass panel with lettering to indicate general game information including, for example, a game denomination (e.g. $0.25 or $1). The bill validator 30, player-input switches 32, video display monitor 34, and information panel are devices used to play a game on the game machine 2. The devices are controlled by circuitry (See FIG. 4) housed inside the main cabinet 4 of the machine 2. Many possible games, including mechanical slot games, video slot games, video poker, video black jack, video pachinko and lottery, may be provided with gaming machines of this invention.

Figure 1:
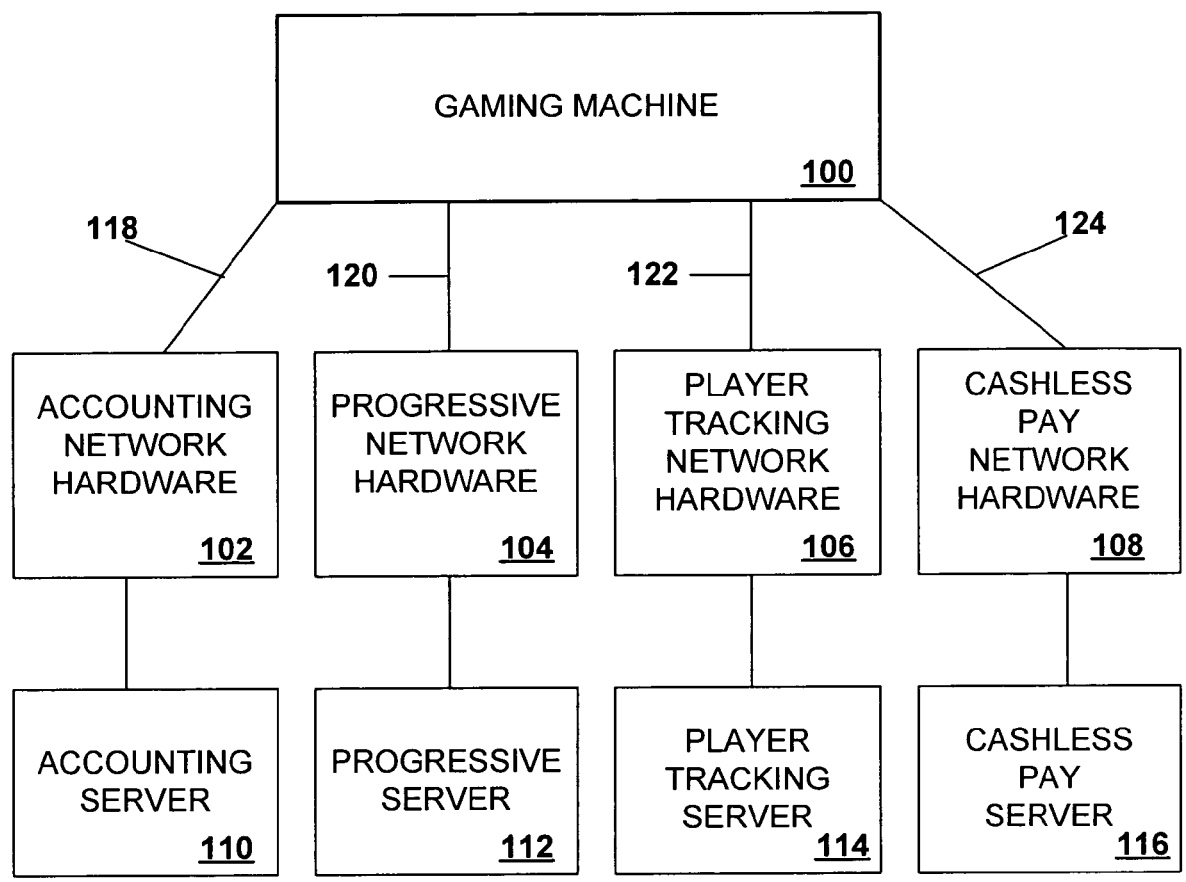
FIG. 1 is block diagram of components used to provide four network game services to a gaming machine in an example of the current gaming network environment.

The gaming machine 2 includes a top box 6, which sits on top of the main cabinet 4. The top box 6 houses a number of devices, which may be used to add features to a game being played on the gaming machine 2, including speakers 10, 12, 14, a ticket printer 18 which prints bar-coded tickets 20, a key pad 22 for entering player tracking information, a florescent display 16 for displaying player tracking information, a card reader 24 for entering a magnetic striped card containing player tracking information, and a video display screen 42. The ticket printer 18 may be used to print tickets for a cashless ticketing system. Further, the top box 6 may house different or additional devices than shown in the FIG. 1. For example, the top box may contain a bonus wheel or a back-lit silk screened panel which may be used to add bonus features to the game being played on the gaming machine. As another example, the top box may contain a display for a progressive jackpot offered on the gaming machine. During a game, these devices are controlled and powered, in part, by circuitry (See FIG. 4) housed within the main cabinet 4 of the machine 2.

Understand that gaming machine 2 is but one example from a wide range of gaming machine designs on which the present invention may be implemented. For example, not all suitable gaming machines have top boxes or player tracking features. Further, some gaming machines have two or more game displays—mechanical and/or video. And, some gaming machines are designed for bar tables and have displays that face upwards. Those of skill in the art will understand that the present invention, as described below, can be deployed on most any gaming machine now available or hereafter developed.

Returning to the example of FIG. 2, when a user wishes to play the gaming machine 2, he or she inserts cash through the coin acceptor 28 or bill validator 30. Additionally, the bill validator may accept a printed ticket voucher which may be accepted by the bill validator 30 as an indicia of credit when a cashless ticketing system is used. At the start of the game, the player may enter playing tracking information using the card reader 24, the keypad 22, and the florescent display 16. Further, other game preferences of the player playing the game may be read from a card inserted into the card reader. During the game, the player views game information using the video display 34. Other game and prize information may also be displayed in the video display screen 42 located in the top box.

During the course of a game, a player may be required to make a number of decisions, which affect the outcome of the game. For example, a player may vary his or her wager on a particular game, select a prize for a particular game selected from a prize server, or make game decisions which affect the outcome of a particular game. The player may make these choices using the player-input switches 32, the video display screen 34 or using some other device which enables a player to input information into the gaming machine. In some embodiments, the player may be able to access various game services such as concierge services and entertainment content services using the video display screen 34 and one more input devices.

During certain game events, the gaming machine 2 may display visual and auditory effects that can be perceived by the player. These effects add to the excitement of a game, which makes a player more likely to continue playing. Auditory effects include various sounds that are projected by the speakers 10, 12, 14. Visual effects include flashing lights, strobing lights or other patterns displayed from lights on the gaming machine 2 or from lights behind the belly glass 40. After the player has completed a game, the player may receive game tokens from the coin tray 38 or the ticket 20 from the printer 18, which may be used for further games or to redeem a prize. Further, the player may receive a ticket 20 for food, merchandise, or games from the printer 18.

Figure 3:
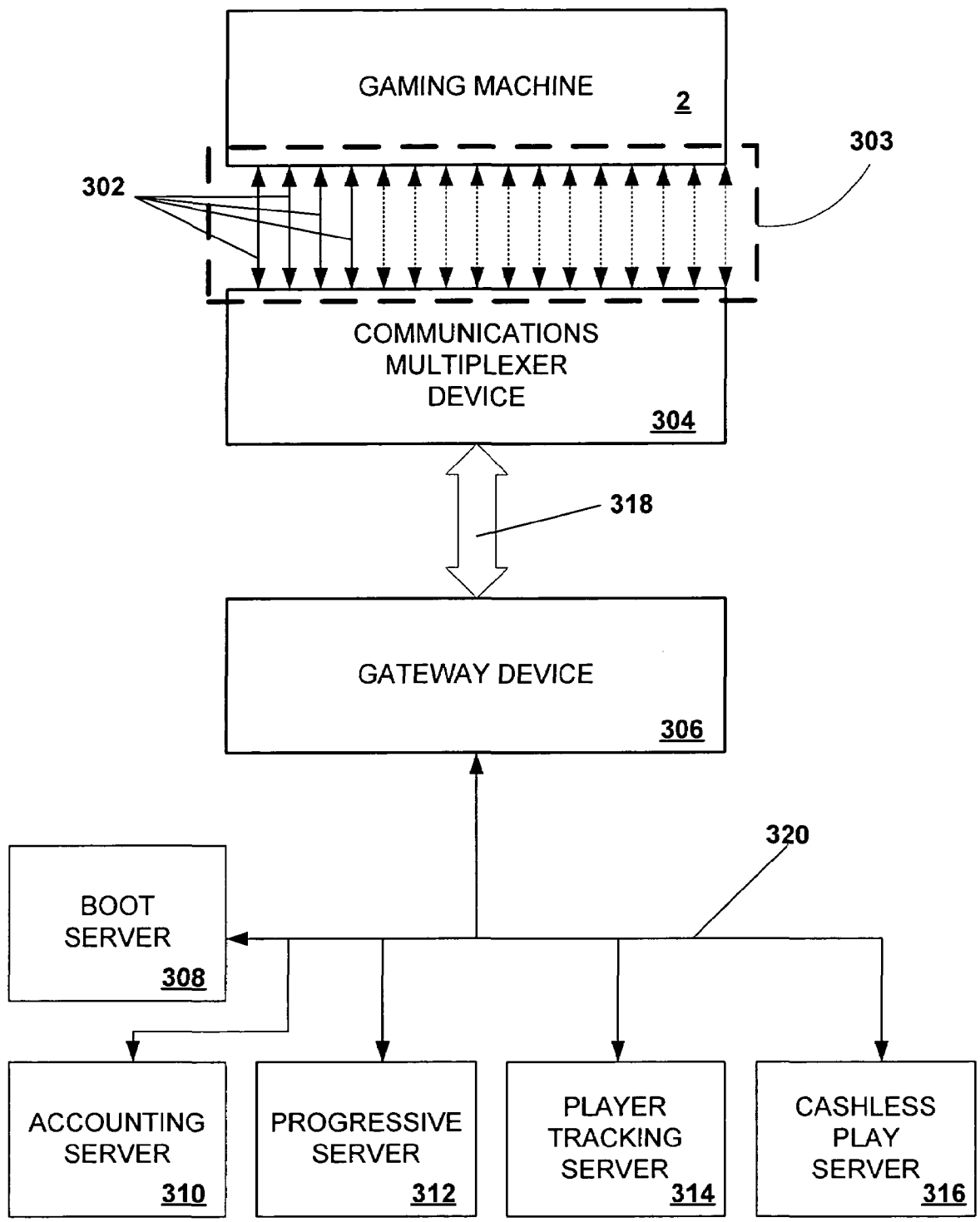
FIG. 3 is a block diagram of a gaming service network employing a communications multiplexer device and a boot server.

FIG. 3 is a block diagram of a gaming service network employing a communications multiplexer device and a boot server. In one embodiment, the gaming machine 2 is connected to the communication multiplexer device 304 via four gaming service network interfaces 302. The communication multiplexer device 304 is outside of the gaming machine in this embodiment but preferably the communication multiplexer device is located inside of the gaming machine 2.

A number of characteristics may be associated with each game service network interface 302 including: 1) a physical interface with a physical communication protocol and 2) an application communication protocol. The physical interface may include parameters such as the cable type, type of pin connectors, signal voltage levels and baud rate while the physical communication protocol may include parameters such as number of stop bits, number of start bits, parity and bits per byte. Asynchronous serial and synchronous serial are common physical communication protocols that may be used with a particular physical interface. Typically, the application protocol is a higher level protocol than the physical communication protocol and is carried over the physical interface using the physical communication protocol. Thus, for instance, a message from the accounting server 310 requesting meter information on the gaming machine, such as "coin in", may be translated into a format consistent with the physical communication protocol and physical interface and transmitted to the gaming machine 2.

RS-422/485, Fiber Optic, RS-232, DCS Current Loop, Link Progressive Current Loop, FIREWIRE, Ethernet and USB are examples of physical interfaces with associated physical communication protocols which may be utilized on one of the game service interfaces 302. RS-422/485 and RS-232 are serial communication protocols established by the Institute of Electronic and Electrical Engineers (IEEE). DCS Current Loop and Link Progressive Current Loop are proprietary communication standards developed by International Gaming Technology, Reno, Nev. Universal Serial Bus (USB) (Communication protocol standards by the USB-IF, Portland, Oreg., http://www.usb.org) is a standard serial communication methodology used in the personal computer industry. FIREWIRE is a cross-platform implementation of the high-speed serial data bus (defined by IEEE Standard 1394-1995) that can move large amounts of data between computers and peripheral devices.

The application protocols sent over each game service network interface 302 are application specific and vary greatly from manufacturer to manufacturer as well as from application to application. For example, a player tracking unit installed in the gaming machine 2 may be used to provide both player tracking information to the player tracking server 314 and accounting information to the accounting server 310. Many different companies manufacture player tracking units including: 1) Acres Gaming, Inc., Las Vegas, Nev., 2) Bally's Gaming Systems, Las Vegas, Nev., 3) Aristocrat, Inc., Reno, Nev., 4) Casino Data Systems, Las Vegas, Nev., 5) Gaming Systems International, Las Vegas, Nev., 6) IGT, Reno, Nev., 7) Mikhon Gaming Corporation, Las Vegas, Nev., 8) Sigma Game, Inc., Las Vegas, Nev., 9) Silicon Gaming, Inc., Palo Alto, Calif., and 10) WMS Gaming, Inc., Chicago, Ill. The application protocol used by each player tracking unit manufacturer to provide player tracking information to the player tracking server 314 and accounting data to the accounting server 310 may be different for each manufacturer. For instance, player tracking units manufactured by IGT may use a Slot Accounting System (SAS) protocol to send messages between the player tracking unit and the accounting server 310 while player tracking units manufactured by Bally's gaming systems may use a Slot Data System (SDS) protocol to send information from the player tracking unit to an accounting server 310. In addition, not all manufactures may use the same protocol to communicate with the accounting server 310 and the player tracking server 314. Further, in some cases the functions of the accounting server 310 and the player tracking server 314 may be executed by the same server.

The application protocol for different network gaming services may be the same or different depending on the manufacturer providing the network gaming service and the type of the network gaming service. For instance, IGT may provide accounting services and player tracking services using SAS, but, may provide progressive game services using a progressive game service protocol different from SAS. In general, the game service network interfaces 302 may carry messages in a number of application specific protocols, including progressive game service protocols, bonus game service protocols, player tracking service protocols, cashless ticketing service protocols, game downloading service protocols, prize service protocols, entertainment content service protocols, concierge service protocols, lottery service protocols and money transfer service protocols.

Application specific protocols, as described above, that are programmed in gaming software residing on the gaming machine 2 and utilized for communications by the gaming machine 2 are referred to as "native communication protocols." All of the different types of application specific protocols may not be native to a particular gaming machine. For instance, in one embodiment, the native communication protocols for gaming machine 2 are an accounting service protocol, a progressive game service protocol, a player tracking service protocol and a cashless ticketing service protocol. In another embodiment for gaming machine, the native communication protocols may include the accounting service protocol, the progressive game service protocol, the player tracking service protocol, the cashless ticketing service protocol, a concierge service protocol and a bonus game service protocol. Thus, the number and type of native communication protocols residing on software in a gaming machine may vary from gaming machine to gaming machine.

Using the native communication protocols and the physical interfaces with the physical communication protocol, messages may be sent between the gaming machine and the communication multiplexer device 304 using the game service network interfaces 302. However, the communication multiplexer device 304 as well as other network hardware such as the gateway device 306 and the local area network 320 may be transparent to the gaming machine 2. Thus, the gaming machine 2 may send a message over one of the gaming service network interfaces 302 assuming it will reach a particular game service server without any knowledge of the network hardware between the gaming machine and the game service server. Additionally, the gaming machine 2 may receive a message from one of the game service servers over one of the network interfaces 302 without knowledge of the network hardware between the gaming machine and the game service server.

In one embodiment, the communication multiplexer device 304 receives messages from the gaming machine 2 (sent to an appropriate game service server) at four communication ports on the communication multiplexer device (see FIG. 5A) where each communication port is connected one of the game service network interfaces 302. The four communication ports are configured to be compatible with the physical interface and physical communication protocol of each game service network interface connected to the port such that the message may be received in a native communication protocol used by the gaming machine. For this invention, the number of game service servers, game service network interfaces and communication ports may vary (e.g. 16 game service servers, 16 game service network interfaces and 16 communication ports 303) and is not limited to four of each.

The communication multiplexer device 304 may multiplex and convert all the messages received at each communication port to a second communication protocol such that the messages from each communication port may be sent via a network interface 318 connected to an output communication port on the communication multiplexer device 304. Messages to all of the game service servers from the gaming machine, including 310, 312, 314, and 316, may be transmitted via the output communication port. For instance, when the communication multiplexer device 304 uses a TCP/IP communication protocol as the second communication protocol, messages received at each communication port may be encapsulated, addressed and sent to the game service server associated with each communication port using the output communication port. The encapsulation, addressing and sending of messages is performed with processor logic stored on the communication multiplexer device. When the communication multiplexer device 304 is initialized with the TCP/IP communication protocol, each communication port may be mapped to a particular gaming service server which allows the communication multiplexer device to route messages received at each communication port to a particular game service server. The initialization process is described with reference to FIG. 6.

Figure 5A:
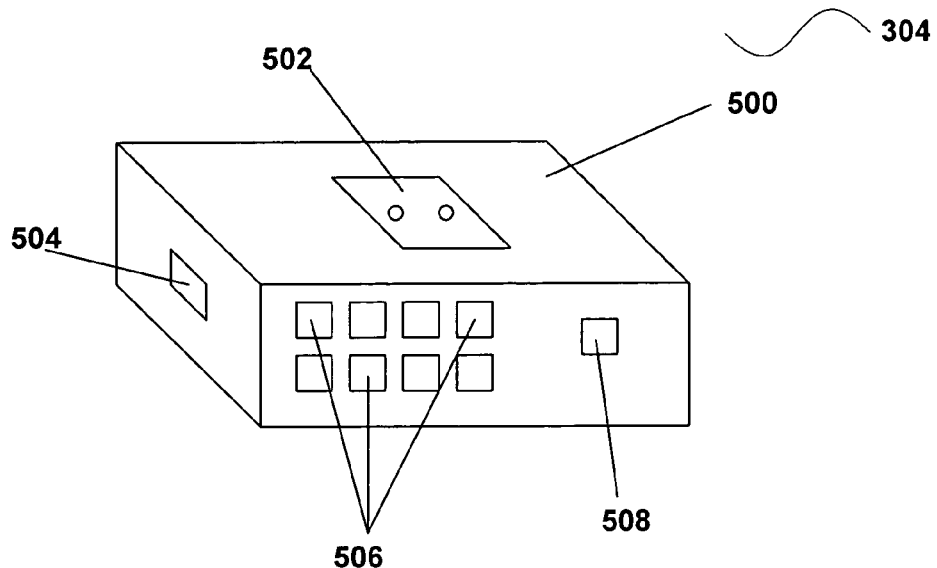
FIGS. 5A and 5B are block diagrams of a communication multiplexer device.

The communication multiplexer device 304 may receive messages from the four game service servers via the network interface 306 at the output communication port (See FIG. 5A)

on the communication multiplexer device 304 in the second communication protocol. Using processor logic, the communication mutliplexer device 304 may demultiplex the messages, determine a destination communication port for each message, convert the message to the native communication protocol associated with each port and send each message to the destination communication port. For instance, when TCP/IP communication protocol is the second communication protocol and the accounting server 310 and the gaming machine 2 communicate using a TCP/IP protocol using port #1 of the communication multiplexer device, the accounting server may encapsulate a message in SAS for the gaming machine 2 and send it to the communication multiplexer device 304. When the communication mutliplexer device 304 receives the message at the output communication port, the communication multiplexer device may unencapsulate the message and send it in the SAS protocol to the gaming machine 2 using port #1.

In another embodiment, the communication multiplexer device may provide translation functions between a gaming machine 2 with a native communication protocol different from the communication protocol used by the game service server. For example, on gaming machine 2, the native communication protocol for accounting game services may be SDS while the accounting game server 310 may use SAS. Thus, when the communication multiplexer device 304 receives a message from the gaming machine 2 at one of the communication ports for the accounting server 310, the communication multiplexer device may convert it from SDS to SAS and then to another format such as TCP/IP (as described above) for transmission to the accounting server 310. Further, when messages are received from the accounting server in SAS, the communication multiplexer device 304 may convert messages from SAS to SDS before transmitting the messages to the gaming machine.

While performing various communication functions, the communication multiplexer device 304 may convert and route messages without interpreting the contents of the messages. Thus, the communication multiplexer may convert and route an encrypted message from a game service server to the gaming machine 2 without decrypting the message. For example, using TCP/IP communication protocol, the encrypted message from the game service server may be received as a payload of an encapsulated message at the communication multiplexer device 304. The encrypted message may be unencapsulated and forwarded to one of the communication ports and then decrypted at the gaming machine. Also, as part of the message conversion process, the communication multiplexer device 304 may be used to encrypt messages. For example, before sending a message to one of the gaming service servers using the wireless radio connection, the communication multiplexer device may encrypt the message.

Messages may be sent from the communications multiplexer device 304 through a single network interface 318 connected to the output communication port. The network interface 318 may be a wireless radio connection, a wired Ethernet connection or any other communication medium allowing communication between the gateway device 306 and the communications multiplexer device 304. When a wireless radio connection is used, an antenna may be connected to the communication multiplexer device 304 for transmitting and receiving messages. The wireless radio connection may utilize wireless communication standards such as IEEE 802.11a or IEEE 802.11b which operate in within various specific frequency bands. For instance, IEEE 802.11a defines a "frequency-hopping spread spectrum" signal modulation technology while IEEE 802.11b defines a "direct-sequence spread-spectrum" signal modulation technology.

In one embodiment, the network interface 318 may be a spread spectrum cellular network communication interface, Spectrum 24, manufactured by Symbol Technologies of Holtsville, N.Y., which operates between about 2.4 and 2.5 GigaHertz. For this embodiment, the high frequency range may provide reliable communications in an electrically noisy casino environment while eliminating the need for communication interconnection by physical wire and cabling. When the single network interface 318 is a wired Ethernet connection, different wired connection schemes such as fiber optic cables, coaxial cables or twisted pair cables may be employed between the gateway device 306 and the communication multiplexer device 304. One advantage to minimizing the number of wire connections between the gaming machine 2 and the game service servers or eliminating the wire connections is simplifying the process of reconfiguring gaming machines on a casino floor.

The gateway device 306 connects to a LAN 320 containing the accounting server 310, progressive server 312, player tracking server 314, the cashless player server 316 and the boot server 308. When 318 is a wired Ethernet connection, the gateway device 306 may be a router manufactured by CISCO technologies, San Jose, Calif. In one embodiment, when 318 is a wireless radio connection, the gateway device may be a transmitter or bridge device installed in the ceiling of the casino. The LAN 320 may use a wire connection scheme, a wireless connection scheme or combinations of wireless and wire connection schemes to connect the game service servers and the boot server The present invention is not limited to the network configuration in FIG. 3. For instance, multiple gateway devices (e.g. bridges and/or routers) and many different gaming machines may comprise the game service network in FIG. 3.

Figure 6:
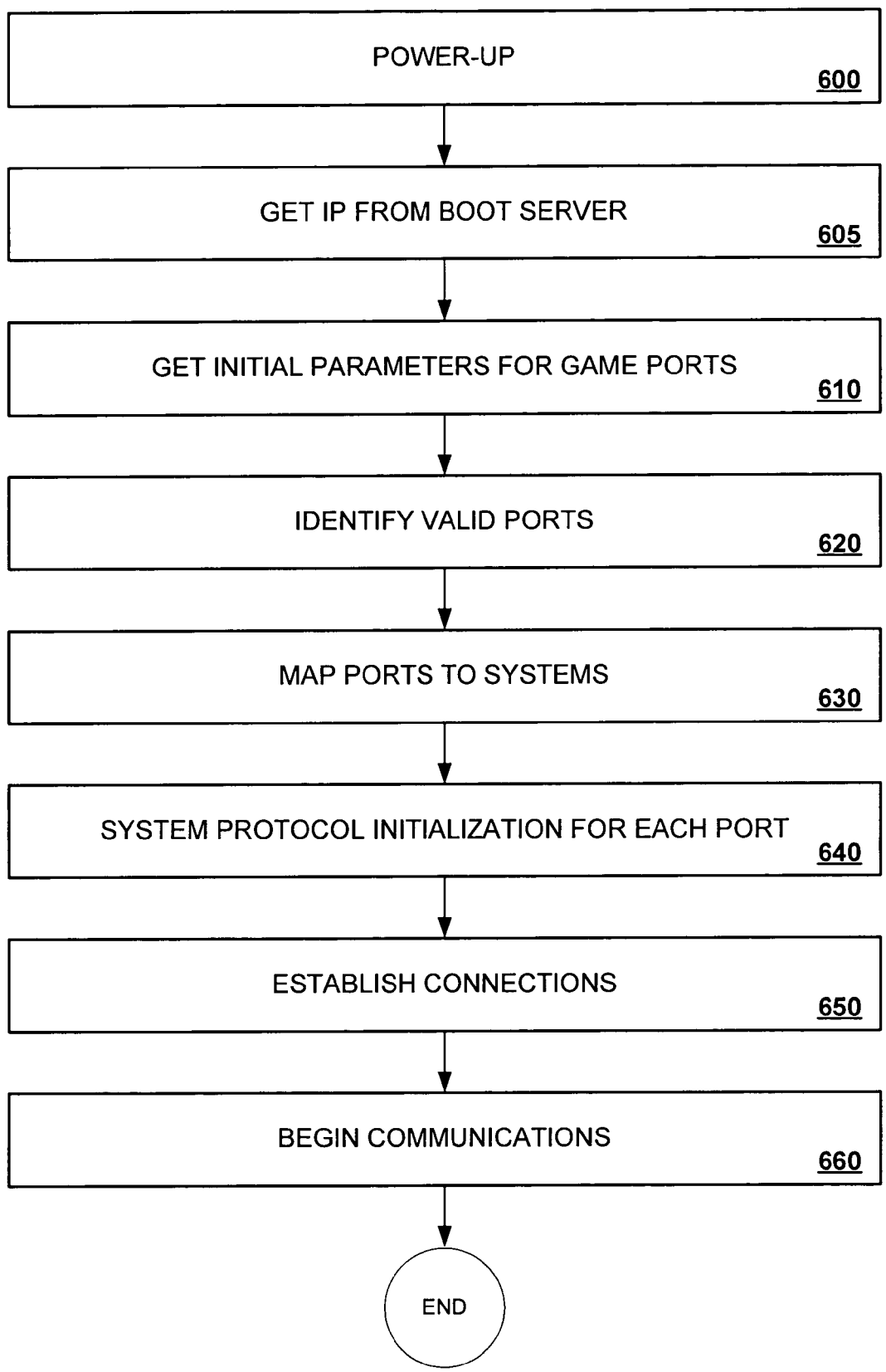
FIG. 6 is a flow chart depicting a method providing communications between a gaming machine and one or more game service servers using a communication multiplexer device.

The boot server 308 may be used to initialize one or more communication multiplexer devices (SEE FIG. 6). For instance, when the communication multiplexer device 304 first powers-up, the communication multiplexer device 304 may send information to the boot server 308 requesting configuration information such as an IP address. After an IP address is assigned to the communication multiplexer device 304, the device may request configuration information such as the number and types of game service servers that may communication with the gaming machine 2. With the configuration information, the communication multiplexer device 304 configures itself to allow communications between the game service servers and the gaming machine 2.

Using a communication multiplexer device 304 that multiplexes messages in communication protocols native to the gaming machine but is transparent to the gaming machine allows for the number of wired connections from the gaming machine to be reduced or eliminated without modifying software on the gaming machine. Advantages to reducing the number of wired connections include decreased gaming server network installation costs, maintenance costs and operation costs. An advantage of reducing the number wires without modifying software on the gaming machine are eliminating significant costs associated with modifying software on the gaming machine and then submitting the software for re-approval.

When new gaming software is developed, that gaming software is typically submitted, for approval, to an official approval agency of each gaming jurisdiction in which the gaming software will be used. The new gaming software is evaluated by each official approval agency according to rules established in the gaming jurisdiction of the agency. Gaming machine software that is regulated by a gaming jurisdiction may be referred to as "regulated gaming software." Nearly all gaming jurisdictions regulate gaming machine software. When gaming software is approved in most jurisdictions, a unique signature is devised for the regulated gaming software and the gaming signature is registered with the jurisdiction. The unique signature is used to insure gaming software installed on a gaming machine has been approved. Usually, the signature for the gaming software on each gaming machine is inspected after is shipped to a particular gaming jurisdiction to determine whether the signature for the gaming software matches a gaming signature approved for the gaming machine. A gaming machine with an invalid signature is not allowed to operate. This procedure, which may be time consuming and expensive, may be required each time software is modified on the gaming machine.

For instance, for many gaming machines currently operating (nearly 700,000), most of the software on the gaming machines may be provided on EEPROMs where the software on the EEPROMs allows the master gaming controller to provide all gaming functions on the gaming machine such as game play and communications. Using EEPROMs, a gaming machine may be used to provide many different games. However, a different EEPROM may be used for each game. When new gaming software for an EEPROM is developed, it is submitted for testing and approval. After the gaming software is approved, it is typically burnt onto the EEPROM.

The number of bits stored on the EEPROM may be summed in some manner to provide a unique signature for each type of EEPROM. The signature for each type of EEPROM may be registered with each gaming jurisdiction. When a gaming machine with a particular EEPROM arrives in a particular gaming jurisdiction, the EEPROM is tested to verify its authenticity against a registered game signature for the EEPROM using a testing device of some type. When the signature for the tested EEPROM does not compare with the registered signature for the EEPROM, the EEPROM may not be used. Hence, the gaming machine using the EEPROM may not be operated until an approved EEPROM is installed in the gaming machine.

Some communication functions provided by the multiplexer communication device 304, such as protocol conversion, could be provided by modifying software on the gaming machine. However, since each time the software on an existing gaming machine is modified it must be submitted for re-approval, this approach may be impractical. For instance, in the example above, a new EEPROM with additional communication software could be developed and installed on a gaming machine after the EEPROM passed the approval and inspection process. Currently, nearly 700,000 gaming machines are being utilized in jurisdictions where gaming software is regulated. The installation of new communication software on all of these gaming machines might cost hundreds of millions of dollars. Further, the process would have to be repeated each time new communication software was installed. Thus, since the communication multiplexer device described in this invention provides additional communication capabilities to the gaming machine without modifying regulated gaming software on the gaming machine, an advantage of using the communication multiplexer device to provide communication functions may be reduced costs associated with re-approval of software on the gaming machine.

Figure 4:
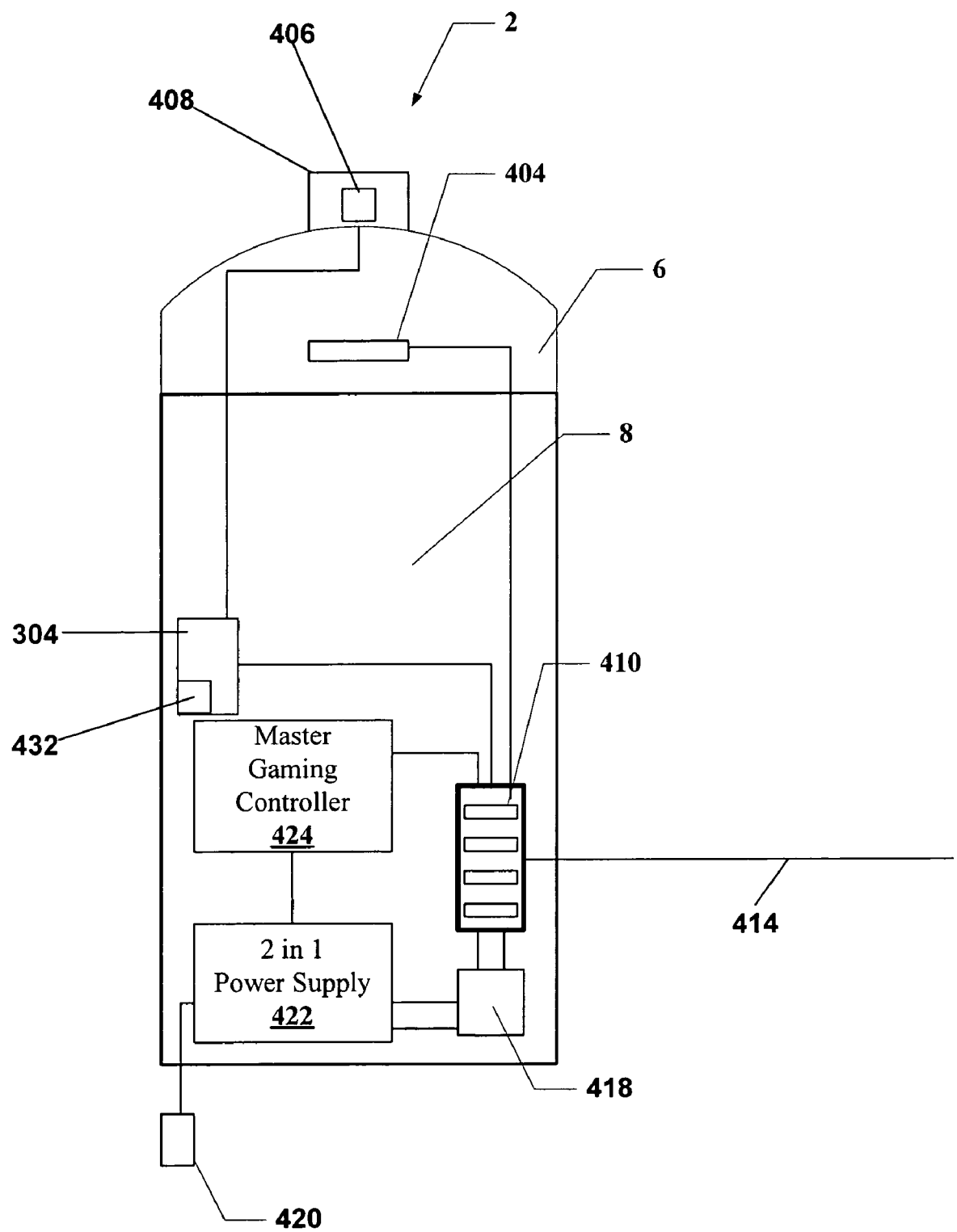
FIG. 4 is a block diagram of a gaming machine connected to a communications multiplexer device.

FIG. 4 is a block diagram of a gaming machine connected to a communications multiplexer device. The gaming machine 2 is comprised of a top box 6 mounted on top of the gaming machine and a main cabinet 8. The gaming machine may be connected to an AC Power source 420. The AC power source 420 provides the power necessary to operate the gaming machine. The AC power source 420 may be connected to a "2 in 1" power supply 422. The "2 in 1" power supply 422 may provide an uninterruptible power source and an interruptible power source. These two power sources may be distributed to various gaming components via the power distribution board 418. Power for various gaming peripherals within the gaming machine may be obtained through a main communication board 410 which is connected to the power distribution board 418. For instance, the communication multiplexer device 304 and the player tracking unit 404 may be connected to the main communication board and receive power via the connection with the main communication board 410 In addition, the communication multiplexer device 304 may utilize a separate DC power supply 432.

The main communication board 410 may be utilized by the master gaming controller 424 to communicate with devices outside of the gaming machine such as game service servers described with reference to FIG. 3 or devices within the gaming machine 2 which the master gaming controller 424 does not directly control. The master gaming controller 424 does not directly control the player tracking unit 404 and the communication multiplexer device 304. Thus, the master gaming controller 424 communicates with these devices using the main communication board 410 as a communication interface. Further, when the communication multiplexer device 304 or the player tracking unit 404 are located outside of the gaming machine 2, the master gaming controller may communicate with these devices using the main communication board 304 in the same manner as when the devices are mounted within the main cabinet 8 of the gaming machine 2. A more complete discussion of the main communication board, which may be used in one embodiment of the present invention, is provided in commonly assigned, co-pending U.S. patent application Ser. No. 09/618,365 CONFIGURABLE HOT-SWAP COMMUNICATION filed Jul. 18, 2000, the entire specification of which is incorporated herein by reference.

The communication multiplexer device 304 may receive all messages transmitted by the gaming machine 2 via the main communication board 410 used by the gaming machine and may receive all messages sent to the gaming machine from outside devices such as game service servers. The communication multiplexer device 304 may operate on the messages to provide various communication functions as described with reference to FIG. 3. For instance, the communication multiplexer device may transmit and receive messages using a wireless radio connection. The antenna 406, which in one embodiment may be mounted within a candle 408 on the gaming machine 2, may be used to send messages to a gateway device as described with reference to FIG. 3. The candle 408 is a type of light which may be mounted on the top of the gaming machine 2. It is noted that the present invention is not limited for use with a main communication board 410 and may be connected to any appropriate interface on the gaming machine.

The communication multiplexer device 304 may not necessarily filter all of the outgoing and incoming communications to the gaming machine 2. For example, in one embodiment, the gaming machine 2 may send and receive messages via the fiber optic network interface 414 for progressive game services. The fiber optic network interface 414 may not be routed through the communications multiplexer device 304. Thus, various combinations of communication for the gaming machine may routed through the communications multiplexer device 304 and other devices such as the fiber optic network interface 414.

Figure 5B:
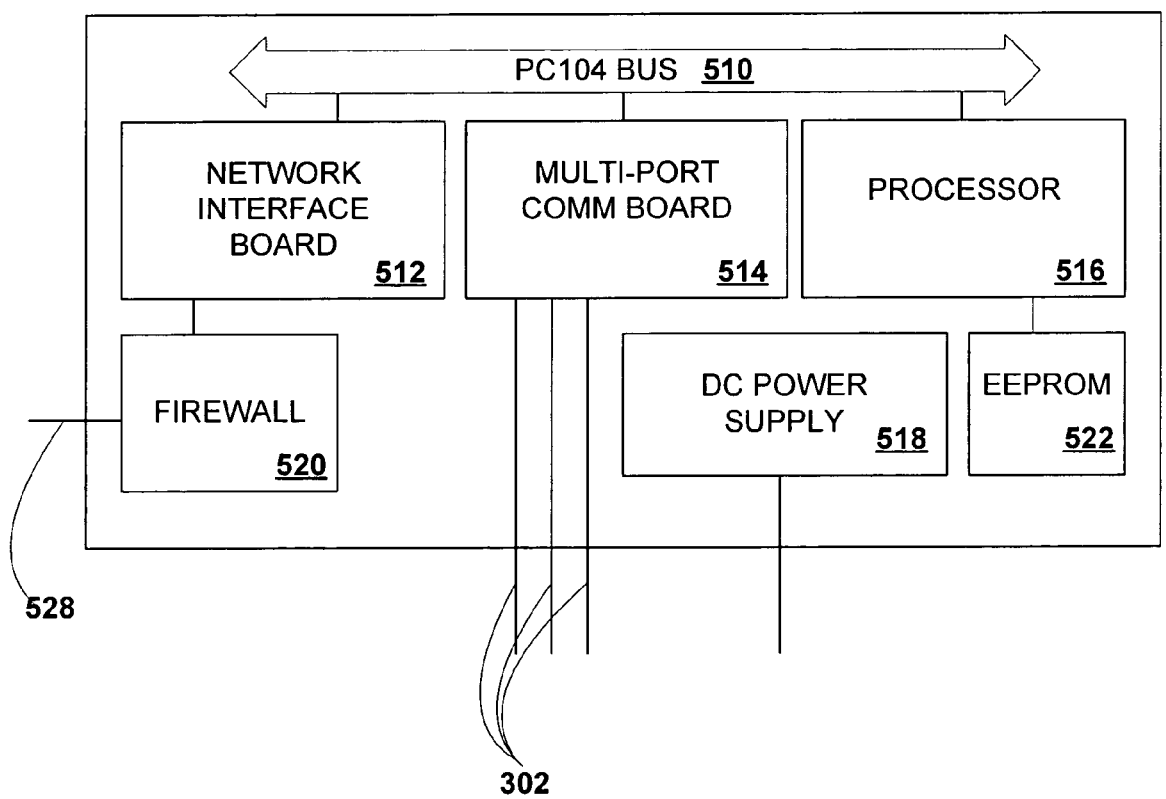

FIGS. 5A and 5B are block diagrams of a communication multiplexer device. FIG. 5A presents the outside of the communication multiplexer device 304. In one embodiment, the communication multiplexer device may be encased within a rectangular enclosure 500. The dimensions of the rectangular enclosure 500 may be about 3-5 inches high, about 4-6 inches wide and about 7-9 inches long. However, the dimensions of the enclosure 500 may be varied to satisfy mounting and space requirements that differ between gamines machine. For instance, one model of a gaming machine may require a different enclosure size because of space restrictions within the gaming machine than another model of a gaming machine. The enclosure 500 may include a mounting bracket 502 for mounting the communication multiplexer device 304 to a surface such as a surface within the main cabinet of a gaming machine.

The enclosure 500 may contain a number of cut-outs for power interfaces and communication interfaces. A power interface 504 may be placed on one surface of the enclosure. An output communication port 508 and eight communication ports 506 are placed on the front of the enclosure. The communication ports 508, as described with reference to FIG. 3, may be designed to accommodate different physical interfaces and the number of communication ports may be varied. For example, in one embodiment, the communication multiplexer device 304 utilizes 16 communication ports.

FIG. 5B is a block diagram of components used in the communication multiplexer device 304. The device 304 may contain a separate DC power supply 518. The multi-port communication board 514 may receive communications from a number of game service interfaces 302 connected into each communication port 506. When the communication multiplexer is initialized, each communication port 506 may be configured by the processor 516 to allow communications with a particular game service interface 302. In one embodiment, communications between the processor 516, the multi-port communication board 514 and the network interface board 512 may be transmitted over a PC104 Bus 510.

As described with reference to FIG. 3, each communication port 506 may be configured for a particular physical communication protocol that allows messages to be communicated in a particular application protocol. For instance, when a particular game service interface utilizes an asynchronous serial physical communication protocol, a processor 516 may configure a port on the multi-port communication board 514 to accept a certain baud rate, number of stop bits, number of stop bits and type of parity (e.g. none, odd, even and wake-up) which allow the communication multiplexer device 304 to receive communications from the gaming machine in a native communication protocol. In addition, the port may be provided a port number and host IP number which allows a game service server or some other device located outside of the gaming machine to address messages to a particular port on the communication multiplexer device 304. As another example, a port may be configured by the processor 516 to use a synchronous serial physical communication protocol. In this case, the bit rate, protocol type, Host IP address, CRC yes/no, CRC type and port number may be configured for the port.

The ports on the multi-port communication board 514 may be reconfigurable. Thus, at one time, a first port on the multi-port communication board 514 may be configured as an asynchronous serial port and at a later time the first port may be configured as a synchronous serial port. Further, each port may be configured to transmit a different native communication protocol from the gaming machine. Thus, a first port may receive an accounting service protocol, while a second port may receive a concierge service protocol, and a third port may receive a bonus game protocol. Also, the first port may be used to communicate with an accounting server, while the second port may communicate with a concierge server and the third port may communicate with a bonus game server. The processor 516 may obtain configuration information for each port from data stored in the EEPROM 522. In another embodiment, the processor board may obtain port configuration information from a boot server (see FIG. 3) located outside of the gaming machine.

In addition, the EEPROM 522 may contain all of the processor logic used by the processor 516. For instance, the EEPROM 522 may contain processor logic allowing the processor to convert messages from one protocol to another protocol such as from a native communication protocol of the gaming machine to a second communication protocol such as TCP/IP. As another example, the EEPROM 522 may contain processor logic allowing the processor to encrypt messages.

The network interface board 512 allows the communication multiplexer device 304 to utilize a particular network interface 528. For example, the network interface may be a wired Ethernet connection or wireless radio connection where communication with the network interface 528 is enabled by the network interface board 512. For security purposes, a firewall 520 may be placed between the network interface board and the network interface 528. The internal firewall may be hardware, software or combinations of both that prevent illegal access of the gaming machine by an outside entity connected to the gaming machine. For instance, an illegal access may be an attempt to plant a program in the gaming machine that alters the operation of the gaming machine using a wireless radio connection into the communications multiplexer device 304. The internal firewall is designed to prevent someone such as a hacker from gaining illegal access to the gaming machine and tampering with it in some manner.

FIG. 6 is a flow chart depicting a method providing communications between a gaming machine and one or more game service servers using a communication multiplexer device. In 600, the communication multiplexer device is connected to a power supply. The communication multiplexer may be connected to the power supply on a gaming machine such that, when the gaming machine is powered-up, the communication multiplexer device is also powered-up. In 605, in one embodiment, after internal self checks, the communication multiplexer device may attempt to contact a boot server using a TCP/IP protocol and obtain an IP address. To obtain an IP address, the communication multiplexer device may send a MAC (medium access control) address to the boot server. After authentication of the MAC address by the boot server, the boot server may assign the communication multiplexer device an IP address.

After receiving an IP address from the boot server, in 610, the communication multiplexer device may get initial parameters for the communication ports. In one embodiment, the parameters may be obtained from the boot server. For instance, the boot server may transmit a configuration file containing the parameter information to the communication multiplexer device. In another embodiment, the configuration file for the communication multiplexer device may be stored on the communication multiplexer device, for example, on an EEPROM. In 620, from the configuration file, the communication multiplexer device identifies valid ports. All ports on the communication multiplexer device are not necessarily utilized. For example, the communication multiplexer device may contain 16 ports where only 5 are utilized.

In 630, the ports are mapped to different systems or devices such as game service servers. In general, any device capable of TCP/IP communications may communicate with a communications multiplexer device. For instance, port 1 may communicate with an accounting server, port 2 may communicate with a bonus game server, port 3 may communicate with a concierge service server and port 4 may communicate with a cashless ticketing server. In 640, a physical communication protocol (e.g. asynchronous serial or synchronous serial) is set for each port. The physical communication protocol allows messages in the application protocol to be transmitted using the communication port. In 650, the communication multiplexer device establishes a connection between each port and the device associated with the port. For example, when port 2 communicates with a bonus game server, then communication between the bonus game server and port 2 is established. In 660, after establishing communications between the ports and devices associated with each port, the communication multiplexer device may be used as a conduit for communications between each device and the gaming machine.

Although the foregoing invention has been described in some detail for purposes of clarity of understanding, it will be apparent that certain changes and modifications may be practiced within the scope of the appended claims. For instance, while the gaming machines of this invention have been depicted as having top box mounted on top of the main gaming machine cabinet, the use of gaming devices in accordance with this invention is not so limited. For example, gaming machine may be provided without a top box.

What is claimed is:

1. A gaming machine comprising:
  a master gaming controller designed or configured i) to control a game of chance played on the gaming machine by executing regulated gaming software, ii) to receive wagers on an outcome for the game of chance and iii) to communicate with one or more game service servers providing game services using one or more application specific protocols included in the regulated gaming software;
  a display for displaying the game of chance played on the gaming machine;
  a communication multiplexer device comprising:
    a plurality of communication ports connected to a multiport communication board wherein each communication port transmits and receives messages between the gaming machine and the communication multiplexer device in at least one of the application specific protocols used by the master gaming controller and wherein each communication port is configured to accept a physical communication connection compatible with at least one or more of the application specific protocols and wherein each communication port is configurable to utilize a physical communication protocol that allows messages in at least one of the application specific protocols to be parsed by the communication multiplexer device;
    only one output communication port that transmits messages addressed to the one or more game service servers and receives messages from the one or more game service servers addressed to one of the plurality of communication ports using a second communication protocol;
    a logic device that does not directly communicate with the master gaming controller on the gaming machine, said logic device adapted for:
      i) determining a destination device for each message received at one of the plurality of communication ports wherein each message is formatted using one of the application specific protocols, formatting each message in one of the application specific protocols into the second communication protocol and transmitting a message formatted in the second communication protocol via the only one output communication port to the destination device wherein the message formatted in the second communication protocol includes information originally formatted in one of the application specific protocols;
      ii) determining a destination port from among the plurality of communication ports for each message received at the only one output communication port wherein each message received at the only one output communication port is formatted using the second communication protocol, formatting the message received in the second communication protocol into one of the application specific communication protocols that is compatible with the destination port and transmitting the message formatted in one of the application specific protocols via the destination port; and
    a memory device for storing a) information regarding the one or more application specific protocols and the physical communication protocol used at each of the plurality of communication ports, b) the second communication protocol and c) a mapping between each of the plurality of communication ports and one or more of the destination devices, said mapping allowing the logic device to determine the destination device or the destination port for each message received by the communications multiplexer device;
  the physical communication connections connected to each of the plurality of communication ports; and
  a network interface connected to the only one output communication port and a network that receives and transmits messages using the second communication protocol.

2. The gaming machine of claim 1, wherein the game services are selected from group consisting of progressive game services, bonus game services, player tracking services, cashless ticketing services, game downloading services, prize services, entertainment content services, concierge services, lottery services and money transfer services.

3. The gaming machine of claim 1, wherein the network interface provides a wireless connection or a wired connection to the network.

4. The gaming machine of claim 3, further comprising:
  an antenna for transmitting and receiving communications over the wireless connection.

5. The gaming machine of claim 1, wherein the one or more application specific protocols are selected from the group consisting of a progressive game service protocol, a bonus game service protocol, a player tracking service protocol, a cashless ticketing service protocol, a game downloading service protocol, a prize service protocol, an entertainment content service protocol, a concierge service protocol, a lottery service protocol and a money transfer service protocol.

6. The gaming machine of claim 1, wherein the plurality of communication ports comprises a first communication port using a first application specific communication protocol and a second communication port using a second application specific communication protocol.

7. The gaming machine of claim 1, wherein the plurality of communication ports comprises a first communication port that receives and sends messages from a first game service server and a second communication port that receives and send messages from a second game service server.

8. The gaming machine of claim 1, wherein the logic device is further adapted for configuring each of the plurality of communication ports to emulate one of the application specific protocols.

9. The gaming machine of claim 1, wherein the logic device is further adapted for communicating with a boot server that sends configuration information to the communication multiplexer device.

10. The gaming machine of claim 9, wherein the configuration information specifies one or more of the mapping between each of the plurality of communication ports and one or more of the destination devices, a particular application specific protocol to use at one of the plurality of communication ports, a particular physical communication protocol to use at one of the plurality of communication ports or combinations thereof.

11. The gaming machine of claim 1, wherein the one or more game service servers are selected from the group consisting of a prize server, a game server, an entertainment content server, a cashless ticketing server, a progressive game server, a bonus game server, a concierge service server, a lottery server and a money transfer server.

12. The gaming machine of claim 1, wherein the game of chance played on the gaming machine is at least one of a video slot game, a mechanical slot game, a lottery game, a video poker game, a video black jack game, and a video pachinko game.

13. The gaming machine of claim 1, wherein each of the physical communication connections are one or more of the following: RS-422/485 compatible, Fiber Optic compatible, RS-232 compatible, DCS Current Loop compatible, Link Progressive Current Loop compatible, FireWire compatible, Ethernet compatible, USB compatible or combinations thereof.

14. The gaming machine of claim 1, wherein the regulated gaming software in a communication path between the gaming machine and the one or more game service servers is the same as when the communication multiplexer device is not in a communication path between the gaming machine and the one or more game service servers.

15. The gaming machine of claim 1, wherein the logic device is further adapted for translating information received in a first application specific protocol to a second application specific protocol.

16. The gaming machine of claim 15, wherein the first application specific protocol is a first player tracking service protocol and the second application specific protocol is a second player tracking service protocol.

17. A gaming system comprising:
a plurality of gaming machines, each gaming machine comprising:
a master gaming controller designed or configured i) to control a game of chance played on the gaming machine by executing regulated gaming software, ii) to receive wagers on an outcome for the game of chance and iii) to communicate with one or more game service servers providing game services using one or more application specific protocols included in the regulated gaming software;
a display for displaying the game of chance played on the gaming machine;
a communication multiplexer device comprising:
a plurality of communication ports connected to a multi-port communication board wherein each communication port transmits and receives messages between the gaming machine and the communication multiplexer device in at least one of the application specific protocols used by the master gaming controller and wherein each communication port is configured to accept a physical communication connection compatible with at least one or more of the application specific protocols and wherein each communication port is configurable to utilize a physical communication protocol that allows messages in at least one of the application specific protocols to be parsed by the communication multiplexer device;
only one output communication port that transmits messages addressed to the one or more game service servers and receives messages from the one or more game service servers addressed to one of the plurality of communication ports using a second communication protocol;
a logic device that does not directly communicate with the master gaming controller on the gaming machine, said logic device adapted for:
i) determining a destination device for each message received at one of the plurality of communication ports wherein each message is formatted using one of the application specific protocols, formatting each message in one of the application specific protocols into the second communication protocol and transmitting a message formatted in the second communication protocol via the only one output communication port to the destination device wherein the message formatted in the second communication protocol includes information originally formatted in one of the application specific protocols;
ii) determining a destination port from among the plurality of communication ports for each message received at the only one output communication port wherein each message received at the only one output communication port is formatted using the second communication protocol, formatting the message received in the second communication protocol into one of the application specific communication protocols that is compatible with the destination port and transmitting the message formatted in one of the application specific protocols via the destination port; and
a memory device for storing a) information regarding the one or more application specific protocols and the physical communication protocol used at each of the plurality of communication ports, b) the second communication protocol and c) a mapping between each of the plurality of communication ports and one or more of the destination devices, said mapping allowing the logic device to determine the destination device or the destination port for each message received by the communication multiplexer device;
the physical communication connections connected to each of the plurality of communication ports; and
a network interface connected to the only one output communication port and a network that receives and transmits messages using the second communication protocol;

the one or more game service servers;
the network for providing a communication path between the one or more game service servers and the gaming machine.

18. The gaming system of claim 17, further comprising:
a boot server for sending configuration information to the communication multiplexer device.

19. The gaming machine of claim 1, wherein the communication multiplexer device is configured to multiplex the messages received at the plurality of communication ports to transfer the received messages via the only one output communication port.

20. The gaming machine of claim 1, wherein the plurality of communication ports include a first communication port and a second communication port, wherein the first communication port is configured to be compatible with a first physical communication protocol and the second communication port is configured to be compatible with a second physical communication protocol, and wherein the second physical communication protocol is different than the first physical communication protocol.

21. The gaming machine of claim 6, wherein the first communication port is configured to be compatible with the first application specific communication protocol and the second communication port is configured to be compatible with the second application specific communication protocol, and wherein the second application specific communication protocol is different from the first application specific communication protocol.

22. The gaming machine of claim 7, wherein the first communication port is configured to be compatible with the first application specific communication protocol used by the first game service server and the second communication port is configured to be compatible with the second application specific communication protocol used by the second game service server, and wherein the second application specific communication protocol is different from the first application specific communication protocol.

* * * * *